United States Patent [19]

Kleemann et al.

[11] Patent Number: 4,751,298

[45] Date of Patent: Jun. 14, 1988

[54] PRODUCTION OF 1-(3-HYDROXY-PROPYL)-1,4-DIAZEPANE AND 1,4-BIS(3,4,5-TRIMETHOXY-BENZOYLOX-Y)-PROPYL-DIAZEPANE DERIVATIVES THEREOF

[75] Inventors: Axel Kleemann, Muhlheim; Bernd Lehmann, Constance; Klaus Deller, Hainburg, all of Fed. Rep. of Germany

[73] Assignee: Degussa Aktiengesellschaft, Frankfurt am Main, Fed. Rep. of Germany

[21] Appl. No.: 693,344

[22] Filed: Jan. 22, 1985

[30] Foreign Application Priority Data

Feb. 3, 1984 [DE] Fed. Rep. of Germany ....... 3403778

[51] Int. Cl.$^4$ ............................................. C07D 243/08
[52] U.S. Cl. ..................................... 540/575; 540/574; 574/399; 574/365; 558/455
[58] Field of Search .................. 268/239 BC; 540/574, 540/575

[56] References Cited

U.S. PATENT DOCUMENTS 3,532,685 10/1970 Arnold ................................ 540/575
4,068,069 1/1978 Kato ..................................... 540/575

FOREIGN PATENT DOCUMENTS 2355420 7/1984 Fed. Rep. of Germany .
3403778 8/1985 Fed. Rep. of Germany ...... 540/575
62842 7/1968 German Democratic Rep. .
0144591 12/1978 Japan ................................... 540/575
0113771 9/1981 Japan ................................... 540/575
0161377 12/1981 Japan ................................... 540/575
31671 2/1982 Japan .
3110668 7/1982 Japan .

OTHER PUBLICATIONS

Poppeldorf, J. Org. Chem. 26, 131–134 (1961).
Kotelko, Acta Polon. Pharm. 18 171-2 (1961) Abstract.
Kotelko, Acta Polon. Pharm. 19, 215–221 (with English Trans.).
Organic Reactions, pp. 205, 239, vol. 12.

Primary Examiner—Glennon H. Hollrah
Assistant Examiner—W. B. Springer
Attorney, Agent, or Firm—Cushman, Darby & Cushman

[57] ABSTRACT

There is disclosed a process for the production of 1,4-bis-[3-(3,4,5-trimethoxybenzyloxy)-propyl]-diazepane which consists of first reacting 3-aminopropanol with acrylonitrile and subsequently reacting in aqueous solution with formaldehyde and hydrocyanic acid or with formaldehyde and an alkali cyanide in the presence of alkali hydrogen sulfite to form cyanomethyl-(2-cyanoethyl)-(3-hydroxy-propyl)-amine; hydrogenating the thus obtained reaction product in the presence of a hydrogenating catalyst and ammonia to 1 (3-hydroxy-propyl)-1,4-diazepane and reacting the latter compound for example with 3-halogen propanol or with allyl alcohol and introducing two 3,4,5-trimethoxy-benzoyl groups into the thus obtained reaction product by esterification.

5 Claims, No Drawings

PRODUCTION OF 1-(3-HYDROXY-PROPYL)-1,4-DIAZEPANE AND 1,4-BIS(3,4,5-TRIMETHOXY-BENZOYLOXY)-PROPYL-DIAZEPANE DERIVATIVES THEREOF

BACKGROUND OF THE INVENTION

The 1-(3-hydroxy-propyl)-1,4-diazepane group is a component of various medicinally active materials. Therefore, 1-(3-hydroxy-propyl)-1,4-diazepane also serves as starting material for the synthesis of such medicinally active materials (see for example German OS No. 2355420). The customary process for production of 1-(3-hydroxy-propyl)-1,4-diazepane consists in the reaction of 1,4-diazepane (homopiperazine) with allyl alcohol or 3-chloropropanol. Hereby the yields are low and for example amount of 34% or 46%. Besides the isolation of the reaction product is cumbersome and expensive. The greatest disadvantage however, in this process is that there is used as starting material 1,4-diazepane. There are numerous processes for the production of this material, which processes, however, likewise only result in low yields. The best synthesis at present consists of the reaction of ethylenediamine with acrylonitrile and subsequent hydrogenation in the presence of Raney-nickel of the N-(2-cyano-ethyl)-ethylenediamine obtained, (see F. Poppelsdorf and R. C. Mayerly, J. Org. Chem. 26 (1961) page 131). The total yield of 1-(3-hydroxy-propyl)-1,4-diazepane based on N-(2-cyano-ethyl)-ethylenediamine, however, also is only 15% with this process. Furthermore, in this process there must be employed four times the molar amount of ethylenediamine per 1 mole of acrylonitrile in order to suppress the addition of a second molecule of acrylonitrile on the reaction product. The separation of the excess ethylenediamine furthermore is difficult and expensive.

SUMMARY OF THE INVENTION

There has now been found an improved way for the production of the 1-(3-hydroxy-propyl)-1,4-diazepane which is considerably simpler to carry out and besides permits obtaining this compound in considerably better yields (53.5% based on acrylonitrile) than has been previously possible. This new method based on the new compound cyanomethyl-(2-cyano-ethyl)-(3-hydroxy-propyl)-amine which on the one hand can be produced very simply and in very high yields (for example, 99% based on acrylonitrile) from the readily available starting materials 3-aminopropanol, acrylonitrile, formaldehyde and hydrocyanic acid in a 1 step process and on the other hand can be hydrogenated very smoothly with ring clousure to 1-(3-hydroxypropyl)-1,4-diazepane. The very high yield of 87 to 99% based n acrylonitrile in production according to the invention of the new compound cyanomethyl-(2-cyano-ethyl)-(3-hydroxy-propyl)-amine is surprising.

Furthermore unexpected also is the smooth ring closure of the cyanomethyl-(2-cyano-ethyl)-(3-hydroxy-propyl)-amine to the 1,4-diazepane derivative in the hydrogenation. For example, it is known that the unsubstituted cyanoethyl-cyanomethyl-amine under customary hydrogenation conditions is not cyclized to the 1,4-diazepane (see Acta Polon. Pharm., Volume 18, pages 171-2 (1961); Acta Polon, Pharm., Volume 19, pages 215-22 (1962) but there is formed the non-cyclic amine (as main product the N-(2-amino-ethyl)-trimethylenediamine).

Furthermore, in contrast to the known syntheses of 1,4-diazepane using ethylenediamine according to the process of the invention it is no longer necessary to employ the 3-amino-propanol in excess.

Starting from 1-(3-hydroxy-propyl)-1,4-diazepane which at present is readily accessible a further aspect of the invention is a new process for the production of 1,4-bis-[3-(3,4,5-trimethoxybenzoyloxy)-propyl]-diazepane by reacting 1-(3-hydroxy-propyl -1,4-diazepane with 3-halopropanol or with allyl alcohol and introducing into the reaction product thus obtained two 3,4,5-trimethoxy-benzoyl groups by esterifying both hydroxy gorups or introducing in alternating sequence into the 1-(3-hydroxy-propyl)-1,4-diazepane a 3,4,5-trimethoxybenzoyl group by esterifying the hydroxy group and introducing the 3-[3,4,5-trimethoxy-benzoyloxy]-propyl-(1)-group on the second free nitrogen atom of the diazepane ring and in a given case, converting the 1,4-bis-[3-(3,4,5-trimethoxybenzoyloxy)-propyl] -diazepane of formula (I) into a salt. The 1,4-bis-[3-(3,4,5-trimethoxy-benzoyloxy)-propyl]-diazepane is a known medicine (DILAZEP).

More specifically, the invention includes:
1. a process for the production of 1,4-bis-[3-(3,4,5-trimethoxy-benzoyloxy)-propyl]-diazepane of the formula

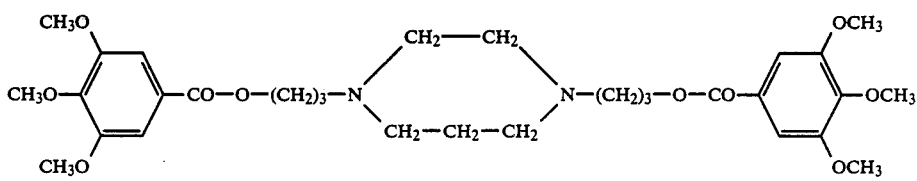

and its salts comprising (a) first reacting 3-amino-propanol with acrylonitrile and subsequently reacting the reaction product obtained (3-(2-cyano-ethyl)-aminopropanol) in aqueous solution with formaldehyde and hydrocyanic acid or with formaldehyde and an alkali cyanide in the presence of alkali hydrogen sulfite to form cyanomethyl-(2-cyano-ethyl)-(3-hydroxy-propyl)-amine;

(b) hydrogenating the cyanomethyl-(2-cyano-ethyl)-(3-hydroxy-propyl)-amine in the presence of a hydrogenation catalyst and ammonia to form 1-(3-hydroxy-propyl)-1,4-diazepane;

(c) reacting 1-(3-hydroxy-propyl)-1,4-diazepane with 3-halopropanol or with allyl alcohol and introducing into the reaction product thus obtained two 3,4,5-trimethoxy-benzoyl groups by esterifying both hydroxy groups or introducing in alternating sequence into the 1-(3-hydroxy-propyl)-1,4-diazepane a 3,4,5-trimethoxybenzoyl group by esterifying the hydroxy group and introducing the 3-[3,4,5-trimethoxy-benzoyloxy]-propyl-[1]-group on the second free nitrogen atom of the diazepane ring and in a given case, converting the 1,4- bis[3-(3,4,5-trimethoxybenzoyloxy)-propyl]-diazepane of formula (I) into a salt.

2. The new compound cyanomethyl-(2-cyano-ethyl)-(3-hydroxy-propyl)-amine of the formula

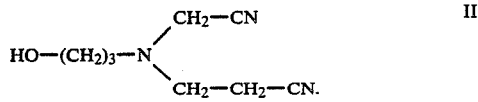

3. A process of producing the cyanomethyl-(2-cyano-ethyl)-(3-hydroxy-propyl)-amine of formula II comprising reacting 2-cyano-ethyl)-(3-hydroxy-propyl)-amine either with formaldehyde and hydrocyanic acid or in the presence of alkali hydrogen sulfite with formaldehyde and an alkali salt of hydrocyanic acid.

4. The compound of formula II is prepared using (2-cyano-ethyl)-(3-hydroxy-propyl)-amine as it is present in the reaction mixture obtained by reaction 3-amino-propanol and acrylonitrile.

5. A process of preparing 1-(3-hydroxypropyl)-1,4-diazepane comprising hydrogenating cyanomethyl-(2-cyano-ethyl)-(3-hydroxy-propyl)-amine in the presence of a hydrogenating catalyst.

6. A process of preparing 1-(3-hydroxy-propyl)-1,4-diazepane comprising hydrogenatingly cyclizing cyanomethyl-(2-cyano-ethyl)-3-hydroxy-propyl)-amine in the presence of a hydrogenation catalyst and ammonia.

The reaction of 3-amino-propanol with acrylonitrile is carried out with stirring or continuously through mixing in equimolar amounts without a solvent at a temperature between 0° and 80° C., preferably 20° to 40° C.

The (2-cyano-ethyl)-(3-hydroxy-propyl)-amine thus obtained (yield 99.5% of theory based on the acrylonitrile) can be used without purification directly for the further cyanomethylation.

It should be understood that the (2-cyano-ethyl)-(3-hydroxy-propyl)-amine primarily obtained from 3-amino-propanol and acrylonitrile also can be isolated and then be reacted with formaldehyde and an alkali salt of hydrocyanic acid (e.g. potassium cyanide or sodium cyanide) in the presence of an alkali hydrogen sulfite (e.g. sodium bisulfite or potassium bisulfite) or with formaldehyde and hydrocyanic acid without addition of alkali sulfite.

Cyanomethylation of the (2-cyano-ethyl)-(3-hydroxy-propyl)-amine:

This reaction is carried out with stirring or continuous thorough mixing of the reactants in aqueous medium at a temperature between 0° and 80°, preferably between 20° and 50° C. In the case where there is used formaldehyde/hydrocyanic acid the reaction is carried out at a pH above 4, preferably 6. There can be used either anhydrous or water containing hydrogen cyanide. The adjustment of the pH is carried out, if necessary, for example with soda lye (NaOH).

In the event a stabilized hydrocyanic acid is used, in a given case, it is necessary to add correspondingly alkali lye (NaOH) in order to neutralize the stabilizer.

Per 1 mole of 3-amino-propanol employed there is used 1.0 to 1.3 moles of hydrocyanic acid. The (2-cyano-ethyl)-(3-hydroxy-propyl)-amine is suitably added in an aqueous solution, which contains formaldehyde 0° and 80° C. The mixture was held 60 to 10 minutes at 20° to 80° C. and then hydrogen cyanide added during 120 to 10 minutes.

In using formaldehyde and an alkali metal salt (e.g. sodium or potassium salt) of hydrocyanic acid the process is carried out in the presence of an alkali hydrogen sulfite, (e.g. sodium or potassium salt).

In place of formaldehyde there can also be used other formaldehyde supplying materials, for example, paraformaldehyde. When paraformaldehyde is used the process is changed as follows: The reaction mixture is stirred until complete dissolution of the paraformaldehyde.

Cyclization of cyanomethyl-(2-cyano-ethyl)-(3-hydroxy-propyl)-amine to 1-(3-hydroxy-proyl)-1,4-diazepane (N-(3-hydroxy-propyl)-homopiperazine:

This hydrogenation reaction is carried out with hydrogen at a temperature between 20°-180° C., preferably 50°-140° C., especially 70°-120° C. and at a pressure between 1-300 bar, preferably 50-150 bar, especially 70-110 bar.

As hydrogenation catalysts there can then be used noble metal catalysts (for example, Pt, Pd, Rh, Ru, PtO$_2$ or mixtures of these catalysts) in free form or as catalysts on carriers (for example on activated carbon, BaSO$_4$, Al$_2$O$_3$) or base metal catalysts, especially Ni or Co catalysts. The base metal catalysts likewise can be used as metals on carriers (for example on SiO$_2$, kieselguhr, Al$_2$O$_3$) or especially in activated form (for example of the Raney type). The amount of catalyst for example can be 1–80%, preferably 2–40%, especially 10–30% of the cyanomethyl-(2-cyano-ethyl)-(3-hydroxy-propyl)-amine.

As solvents for the hydrogenation reaction there can be used for example: water, symmetrical or unsymmetrical alkyl ethers having alkyl groups of 1-6 carbon atoms, e.g. dimethyl ether, diethyl ether, dibutyl ether, methyl hexyl ether, ethyl nonyl ether, saturated cycloaliphatic ethers such as tetrahydrofuran, dioxane, $C_1$-$C_6$-alkanols (e.g. methanol, ethanol, isopropanol, butanol, hexanol), preferably $C_1$-$C_5$-alkanols. These media can also be used a mixtures. The concentration of the cyanomethyl-(2-cyano-ethyl)-(3-hydroxy-propyl)-amine in the solvent for example can be between 0.1–70%, preferably 1–40%. The hydrogenation is carried out in the presence of ammonia. Per 1 mole of cyanomethyl-(2-cyano-ethyl)-(3-hydroxy-propyl)-amine there is used for example 0–50 moles of NH$_3$, preferably 0.1–30 moles of NH$_3$, especially 1–15 moles of NH$_3$.

The cyanomethyl-(2-cyano-ethyl)-(3-hydroxy-propyl)-amine is also especially suited as crude product (that is for example contaminated by acrylonitrile) for the hydrogenation. In such case then it is suitable to use a highly active catalyst, as for example, a freshly produced catalyst (for example freshly produced Raney-nickel).

On the other hand, if there is employed pure, that is recrystallized cyanomethyl-(2-cyano-ethyl)-(3-hydroxy-propyl)-amine, then it is frequently recommended in this case to employ for the hydrogenation a less active catalyst, such as for example, commercial Raney-nickel.

For step (c) of process 1 above:

The reaction of 1-(3-hydroxy-propyl)-1,4-diazepane with 3-halopropanol (halogen preferably chlorine or bromine) can be carried out without solvent or in the presence of a solvent substantially inert to 1-(3-hydroxy-propyl)-1,4-diazepane and 3-chloropropanol.

If the process is carried under normal pressure, then the solvent used or mixture of solvent must have a boiling point which awt least corresponds to the reaction temperature. As solvent there can be used for example, lower aliphatic alcohols (e.g. methanol, ethanol, propanol, isopropanol, n-butanol), aromatic hydrocarbons such as toluene and xylene, cyclic ethers such as dioxane, saturated aliphatic ethers such as ethylene glycol dimethyl ether. The reaction temperature can be between 60° and 170° C., preferably between 90° and 130° C. The reaction time decreases with increasing temperature.

The reaction of the 1-(3-hydroxy-propyl)-1,4-diazepane with 3-chloropropanol can be carried out in the absence or presence of a helping base. In the absence of a base there is obtained the 1,4-bis-(3-hydroxy-propyl)-1,4-diazepane as the monohydrochloride. As helping base there can be used organic and inorganic bases. Preferably, there are used bases whose chlorides are insoluble in the reaction mixture and can be separated off by filtration, such as for example, potassium carbonate, sodium carbonate or sodium methylate.

Per mole of 1-(3-hydroxy-propyl)-1,4-diazepane there are employed 1 to 1.5 moles of 3-chloropropanol and 0 to 1.5 moles of helping base.

In place of 1-(3-hydroxy-propyl)-1,4-diazepane there can be used a salt of the same, especially the dihydrochloride. In this case there is needed at lest the equivalent amunt of helping base.

The reaction of the 1-(3-hydroxy-propyl)-1,4-diazepane with allyl alcohol can be carried out with or without solvent. However, preferably, except for allyl alcohol itself, no solvent is used. The reaction is catalyzed by strong bases, especially alkali alcoholates such as sodium allyl alcoholate, alkali oxides, e.g. sodium oxide and potassium oxide and alkali hydroxide, e.g. sodium hydroxide and potassium hydroxide.

The reaction temperature can be between 80° and 190° C., preferably between 95° and 160° C. At reaction temperatures above the boiling point of allyl alcohol the process is carried out under pressure up to 13 bar. The reaction time decreases with increasing temperature.

Esterification or acylation of the 1,4-bis-(3-hydroxy-propyl)-1,4-diazepane:

The acylation can be carried out for example in inert solvents or suspension agents such as aliphatic $C_3$–$C_9$-ketones, e.g. acetone, methyl ethyl ketone, diethyl ketone, methyl heptyl ketone, dioxane, dimethyl formamide, benzene or toluene at a temperature between 0° to 200° C., preferably 20° to 150° C. As acylation agent there can be used acid halides (chloride, bromide, iodide), acid anhydrides or acid esters of the 3,4,5-trimethoxy-benzoic acid or the free acid itself, in a given case, with addition of an acid binding agent such as a tertiary amine, for example, triethylamine or pyridine. Pyridine also can be simultaneously used as solvent. With esters there are especially used those with lower aliphatic alcohols, e.g. methanol, ethanol, isopropanol. In the acylation it is also possible to proceed by first producing an alkali compound of the compound being reacted, by reacting it with an alkali metal, alkali hydride or alkali amide (especially sodium or sodium compounds) in an inert solvent such as dioxane, dimethyl formamide, benzene or toluene at a temperature between 0° and 150° C. and then to add the acylating agent.

In case the free acid is used, then there is necessary activation through the presence of condensation agents such as dicyclohexylcarbodiimide, sulfurous acid bis alkylamides (for example $SO[N(CH_3)_2]_2$, N,N'-carbonyldiimidazole etc), Organic Reactions, Volume 12, 1962, pages 205 and 239.

In another embodiment the hydroxy group of the 1-(3-hydroxy-propyl)-1,4-diazepane can first be esterified with the 3,4,5-trimethoxy-benzoic acid and subsequently the second free NH-group of the 1,4-diazepane ring be alkylated by the 3-[3,4,5-trimethoxy-benzoyloxy]-propyl group. These two reactions naturally can also be carried out in reverse sequence.

The esterification with the 3,4,5-trimethoxy-benzoic acid proceeds advantageously in the presence of a dehydration agent, such as for example, hydrochloric acid, sulfuric acid, p-toluenesulfonic acid, dicycloheylcarbodiimide, sulfurous acid-bis-alkylamides, N,N'-carbonyldiimidazole, etc., whereby the use of p-toluenesulfonic acid is especially preferred. In the esterification of the invention there can be used any desired solvent insofar as it does not hinder the reaction. Typical examples for solvents are: benzene, toluene, xylene, dioxane, chloroform, tetrahydrofuran, etc., whereby toluene or dioxane is preferred. The reaction temperature generally is advantageously above room temperature, expecially preferred is near the boiling point of the solvent used.

The subsequent introduction of the 3-[3,4,5-trimethoxy-benzoyloxy]-propyl group is carried out for example by reaction with a 3-[3,4,5-trimethoxy-benzoyloxy]-propyl halide (especially the chloride or bromide) in an inert solvent or suspension agent at a temperature between 50° and 180° C., preferably 70° to 140° C. As solvent and basic adjuvant there can be used those already set forth for the reaction of 1-(3-hydroxy-propyl)-1,4-diazepane with 3-halo-propanol. The other conditions used also are analogous to those mentioned there.

In case the introduction of the 3-[3,4,5-trimethoxy-benzoyloxy]-propyl group is carried out first, the subsequent esterification can be carried out also by reaction with a 3,4,5-trimethoxy-benzoyl halide (preferably chloride or bromide) or an anhydride or acid ester of the 3,4,5-trimethoxy-benzoyl halide.

Unless otherwise indicated all parts and percentages are by weight.

The process can comprise, consist essentiallyl of, or consist of the recited materials.

DETAILED DESCRIPTION

EXAMPLE 1

Synthesis of cyanomethyl-(2-cyano-ethyl)-(3-hydroxy-propyl)-amine:

600.8 grams (8.0 mole) of 3-amino-propanol were treated with 424.5 grams (8.0 moles) of acrylonitrile within 75 minutes at 25° C. The mixture was allowed to further react for 1 hour at 25° C. and then the 3-(2-cyanomethyl)-aminopropanol obtained within 60 minutes at 20° to 40° C. was dropped into 840 grams (8.4 moles) of 30% aqueous formaldehyde solution. In connection with a 30 minute further reaction at 40° C. there were dropped in at the same temperature within 45 minutes 239 grams (8.84 moles) of water-free hydrocyanic acid. The mixture was allowed to react further for 2 hours at 40° C. It was cooled, treated with 800 ml of methylene chloride and the lower organic phase formed separated off. The aqueous phase was extracted again with 250 ml of methylene chloride. After concentration of the combined organic phases there remained 1325 grams (99% of theory based on the acrylonitrile) of a colorless oil, which crystallized at room temperature. M.P. 28°–33° C.

EXAMPLE 2

Synthesis of Cyanomethyl-(2-cyano-ethyl)-(3-hydroxy-propyl)-amine:

There were added to 100 grams (1 mole) of 30% formaldehyde solution within 15 minutes at 30° C. a solution of 109.5 grams (1 mole) of 95% sodium hydrogen sulfite in 190 ml of water. Subsequently, there were dosed in at 40° C. within 30 minutes 128 grams of 3-(2-cyano-ethyl)-aminopropanol. The mixture was allowed to react further for 15 minutes and then treated within 35 minutes at 40° C. with a solution of 78 grams (1.15 moles) of 96% potassium cyanide in 150 ml of water. Subsequent to further reaction for one hour at 40° C., the mixture was cooled to 25° C. and the upper organic phase separated off. The organic phase was taken up in 200 ml of methylene chloride and stirred with 2 grams of activated carbon, 2 grams of kieselguhr and 14 grams of water-free sodium sulfate. After filtration the solvent was distilled off, whereby 146 grams (0.873 mole; 87% of theory based on the acrylonitrile) of cyanomethyl-(2-cyano-ethyl)-(3-hydroxy-propyl)-amine precipitated as a yellowish oil, which crystallized at 22° C.

The recrystallization from ethyl acetate yielded an analytically pure product having a melting point of 36° C. IR: (Film) Bands at: 3440, 2940, 2840, 2240, 1135, 1060 $cm^{-1}$.

EXAMPLE 3

Synthesis of (2-cyano-ethyl)-(3-hydroxy-propyl)-amine:

75 grams (1 mole) of 3-amino-propanol were treated with 53 grams (1 mole) of acrylonitrile within one hour at 25° C. The mixture was allowed to react further for 1 hour at 40° C. The thus obtained reaction product (128 grams) was directly reacted further with formaldehyde/hydrocyanic acid or formaldehyde/alkali salt of hydrocyanic acid in the presence of alkali hydrogen sulfite.

EXAMPLE 4

Synthesis of 1-(3-hydroxypropyl)-1,4-diazepane:

(a) 146 grams (0.873 mole) of cyanomethyl-(2-cyano-ethyl)-(3-hydroxy-propyl)-amine were dissolved in a mixture of 1460 ml of methanol and 365 grams of ammonia. The solution was hydrogenated together with 87 grams of Raney-nickel in an autoclave at 80 bar hydrogen pressure at 80° C. until the end of the absorption of hydrogen (5 hours).

The solution separated off from the catalyst was evaporated, whereby methanol and ammonia were recovered.

The evaporation residue was rectified in a vacuum. As the main course there were obtained 75 grams (54% of theory) of 1-(3-hydroxypropyl)-1,4-diazepane having a boiling point of 97° C. at 0.13 mbar. The refractive index was $N^{20}$–1.5000.

(b) 100 grams (0.0598 mole) of cyanomethyl-(2-cyano-ethyl)-(3-hydroxy-propyl)-amine, 400 ml of isopropanol, 56 grams of ammonia and 24 grams of Raney-nickel were heated for 10 hours under 100 bar hydrogen pressure at 100° C.

The solution separated from the catalyst was evaporated and the residue rectified in a vacuum. As the main course there was obtained 51 grams (54% of theory) as a final product.

(c) 100 grams (0.598 mole) of cyanomethyl-(2-cyanoethyl)-(3-hydroxy-propyl)-amine, 800 ml of ethanol, 67 grams of ammonia and 26 grams of Raney-nickel were heated in an autoclave during 2 hours under 80 to 100 bar hydrogen pressure at 70° C. (at the beginning) to 120° C. (toward the end). Subsequently the reaction mixture was worked up as described under (b). There were obtained 52 grams (55% of theory) as a final product.

EXAMPLE 5

79 grams (0.5 mole) of 1-(3-hydroxy-proyl)-1,4-diazepane were dissolved in 200 ml of n-butanol and treated with 52.0 grams (0.55 mole) of 3-chloropropanol. The mixture was heated to boiling under reflux for 4 hours, then treated with 99 grams (0.55 mole) 30% sodium methylate solution and methanol subsequently distilled over a column. The reaction mixture was cooled and filtered. The filter cake consisting of sodium chloride was post washed with 80 ml of n-butanol. The filtrate was concentrated, whereby n-butanol was recovered.

There remained as residue 108 grams (0.5 mole) of oily 1,4-bis-(3-hydroxy-propyl)-1,4-diazepane. For further purification this can be taken up in a mixture of 720 ml of ethanol and 100 ml of methanol and adjusted to pH 0.5 with 38 grams of hydrogen chloride gas. In the cooling there crystallized out 116 grams (80% of theory) of pure 1,4-bis-(3-hydroxy-propyl)-1,4-diazepane dihydrochloride.

EXAMPLE 6

11.5 grams (0.5 mole) of sodium were dissolved under reflux cooling in 310 grams of allyl alcohol. After addition of 79 grams (0.5 mole) of 1-(3-hydroxy-propyl)-1,4-diazepane the mixture was heated for 80 hours under reflux. The mixture was cooled and 18 grams (0.5 mole) of HCl-gas led in under stirring and cooling. The sodium chloride which separated out was filtered off and post washed with 50 ml of allyl alcohol. The filtrate was concentrated, there remained 101 grams (0.47 mole) of oily 1,4-bis-(3-hydroxy-propyl)-1,4-diazepane. For further purification this can be taken up in a mixture for 720 ml of ethanol and 100 ml of methanol and the pH adjusted to 0.5 with 38 grams of HCl gas.

77 grams (53% of theory) of 1,4-Bis-(3-hydroxypropyl)-1,4-diazepane dihydrochloride crystallized out in the cooling.

The entire disclosure of German priority application P 3403778.0 is hereby incorporated by reference.

EXAMPLE 7

21.6 g of 1,4-bis-(3-hydroxypropyl)-1,4-diazepane and 63.8 g of 3,4,5-trimethoxy benzoic acid chloride are dissolved in 600 parts by volume of anhydrous chloroform. The solution is heated to boiling for 5 hours. Thereafter, chloroform is distilled off in a vacuum. The residue is dissolved in water and the aqueous solution is washed with ether. Thereafter, the aqueous phase is rendered alkaline by the addition of soda lye and the separated oily base is extracted with ether. The ethereal solution is dried over $Na_2SO_4$. Ether is separated in a vacuum and the highly viscous residue is dissolved in 150 parts by volume of ethyl alcohol. The calculated equivalent amount of ethereal HCl is added thereto. The soon crystallizing dihydrochloride is separated by filtration, dried and recrystallized from 120 parts by volume of ethanol. Thus, after drying for 3 days over $P_2O_5$, 45–50 g. (66–70% of the theoretical) of 1,4-bis-[3-(3,4,5-trimethoxy benzoyloxy)propyl]-diazepane dihydrochloride containing 1 mol of water of crystallization is obtained. This product has a melting point at 194°–198° C.

What is claimed is:

1. A process for the production of 1,4-bis-3-hydroxypropyl)-1,4-diazepane comprising:
   (a) first reacting 3-amino-propanol with acrylonitrile and subsequently reacting the 3-(2-cyano-ethyl)-aminopropanol obtained in aqueous solution with formaldehyde and hydrocyanic acid to form cyanomethyl-(2-cyano-ethyl)-(3-hydroxy-propyl)-amine;
   (b) hydrogenating the cyanomethyl-(2-cyano-ethyl)-(3-hydroxy-propyl)-amine in the presence of hydrogenation catalyst and ammonia to form 1-(3-hydroxy-propyl)-1,4-diazepane; and
   (c) reacting 1-(3-hydroxy-propyl)-1,4-diazepane with 3-chloropropanol or 3-bromopropanol or with allyl alcohol.

2. A process according to claim 1 wherein the hydrocyanic acid employed is preformed.

3. A process according to claim 1 wherein the hydrocyanic acid is formed in situ by reaction of formaldehyde with an alkali cyanide in the presence of alkali hydrogen sulfite.

4. A process for producing 1,4-bis-[3-(3,4,5-trimethoxybenzoyloxy)-propyl]-1,4-diazepane comprising:
   (a) first reacting 3-amino-propanol with acrylonitrile and subsequently reacting the 3-(2-cyano-ethyl)-aminopropanol obtained in aqueous solution with formaldehyde and hydrocyanic acid to form cyanomethyl-(2-cyano-ethyl)-(3-hydroxy-propyl)-amine;
   (b) hydrogenating the cyanomethyl-(2-cyano-ethyl)-(3-hydroxy-propyl)-amine in the presence of a hydrogenation catalyst and ammonia to form 1-(3-hydroxy-propyl)-1,4-diazepane;
   (c) esterifying the hydroxy group of 1-(3-hydroxy-propyl)-1,4-diazepane with a 3,4,5-trimethoxybenzoyl group; and
   (d) introducing a 3-[3,4,5-trimethoxy-benzoyloxy]-propyl-(1)-group on the 4 nitrogen of the product of step (c), and optionally converting the resulting 1,4-bis-[3-(3,4,5-trimethoxybenzoyloxy)-propyl]-1,4-diazepane into a salt by reaction with a pharmaceutically acceptable acid.

5. A process for producing the ester, 1,4-bis-[3-(3,4,5-trimethoxy benzoyloxy)propyl]-1,4 diazepane comprising the process steps (a) through (c) as recited in claim 1 and further comprising the step (d) of esterifying the product of step (c) with two 3,4,5-trimethoxy-benzoyl groups and optionally converting the 1,4-bis-[3-(3,4,5-trimethoxybenzoyloxy)-propyl]-1,4-diazepane ester into a salt by reaction with a pharmaceutically acceptable acid.

* * * * *